United States Patent [19]

Brooks et al.

[11] Patent Number: 5,288,743
[45] Date of Patent: Feb. 22, 1994

[54] INDOLE CARBOXYLATE DERIVATIVES WHICH INHIBIT LEUKOTRIENE BIOSYNTHESIS

[75] Inventors: Dee W. Brooks, Libertyville; Keith W. Woods, Lake Forest, both of Ill.; Karen E. Rodriques, Stowe, Mass.

[73] Assignee: Abbott Laboratories, Abbott Park, Ill.

[21] Appl. No.: 979,138

[22] Filed: Nov. 20, 1992

[51] Int. Cl.$^5$ ................. A61K 31/405; C07D 277/04
[52] U.S. Cl. ..................... 514/365; 514/369; 514/414; 514/418; 514/419; 548/181; 548/484; 548/467; 546/273; 514/339
[58] Field of Search ............... 548/182, 187, 203, 204, 548/205, 181; 514/369, 365

[56] References Cited

U.S. PATENT DOCUMENTS

| | | | |
|---|---|---|---|
| 3,859,305 | 1/1975 | Possel et al. | 548/493 |
| 3,931,229 | 1/1976 | Zinnes et al. | 548/189 |
| 4,021,448 | 5/1977 | Bell | 548/493 |
| 4,119,638 | 10/1978 | Ray | 548/500 |
| 4,464,379 | 8/1984 | Betzing et al. | 546/273 |
| 4,556,672 | 12/1985 | Kadin | 514/414 |
| 4,654,360 | 3/1987 | Greenhouse et al. | 514/418 |
| 4,737,519 | 4/1988 | Yamashita et al. | 514/510 |
| 4,814,344 | 3/1989 | Humber et al. | 514/397 |
| 4,824,852 | 4/1989 | Böttcher | 514/290 |
| 4,873,259 | 10/1989 | Summers | 514/443 |
| 4,918,094 | 4/1990 | Bernstein | 514/419 |
| 5,041,460 | 8/1991 | Matassa | 514/419 |
| 5,095,031 | 3/1992 | Brooks | 514/419 |
| 5,120,749 | 6/1992 | Summers | 514/337 |
| 5,130,485 | 7/1992 | Hite | 562/623 |
| 5,132,319 | 7/1992 | Girard | 514/415 |

FOREIGN PATENT DOCUMENTS 0275667 7/1988 European Pat. Off. .
WO91/14674 10/1991 PCT Int'l Appl. .

OTHER PUBLICATIONS

Prasit et al. CA 115:207870x. 1991.

*Primary Examiner*—Jane T. Fan
*Attorney, Agent, or Firm*—Jerry F. Janssen

[57] ABSTRACT

Compounds of the structure

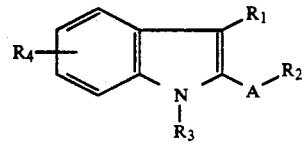

where A is straight or branched divalent alkylene or divalent cycloalkylene, $R_1$ is selected from hydrogen; alkylthio; optionally substituted phenylthio; optionally substituted phenylalkylthio; optionally substituted 2-, 3-, and 4-pyridyl; optionally substituted 2-, and 3-thienylthio; and optionally substituted 2-thiazolythio, $R_2$ is selected from —COOB; —COOalkyl; —COOalkyl(carbocyclic aryl); —CONR$_5$R$_6$; —COR$_6$; and —OH, $R_3$ is selected from phenylalkyl and heteroarylalkyl, and $R_4$ is selected from optionally substituted alkoxy(carbocyclic aryl); optionally substituted carbocyclic aryloxy; optionally substituted heteroarylalkoxy; and optionally substituted heteroaryloxy are potent inhibitors of lipoxygenase enzymes and thus inhibit the biosynthesis of of leukotrienes. These compounds are useful in the treatment or amelioration of allergic and inflammatory disease states.

7 Claims, No Drawings

INDOLE CARBOXYLATE DERIVATIVES WHICH INHIBIT LEUKOTRIENE BIOSYNTHESIS

TECHNICAL FIELD

This invention relates to compounds having biological activity to inhibit lipoxygenase enzymes, to pharmaceutical compositions comprising these compounds, and to a medical method of treatment. More particularly, this invention concerns certain indole carboxylate derivatives which inhibit leukotriene biosynthesis, to pharmaceutical compositions comprising these compounds and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes (Samuelsson, B., "Leukotrienes: Mediators of Immediate Hypersensitivity Reactions and Inflammation," *Science*, 120: 568, 1983; Hammarstrom, S. Leukotrienes, *Annual Review of Biochemistry*, 52: 355, 1983). This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to $LTA_4$. This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described.

Products of the 5-lipoxygenase cascade are extremely potent substances which produce a wide variety of biological effects, often in the nanomolar to picomolar concentration range. (Sirois, P., *Pharmacology of the Leukotrienes, Advances in Lipid Research*, R. Paoletti, D. Kritchevesky, editors, Academic Press, 21: 79, 1985).

Leuokotrienes have been reported to be important mediators in several disease states including: Asthma, Allergic Rhinitis, Rheumatoid Arthritis, Gout, Psoriasis, Adult Respiratory Distress Syndrome, Inflammatory Bowel Disease, Endotoxin Shock, Ischemia-induced Myocardial Injury, Central Nervous Pathophysiology, and Atherosclerosis.

The enzyme 5-lipoxygenase catalyzes the first step leading to the biosynthesis of all the leukotrienes and therefore inhibition of this enzyme provides an approach to limit the effects of all the products of this pathway. Agents capable of abrogating the effects of these potent mediators of pathophysiological processes represent a promising class of therapeutic agents (Brooks, D. W., Bell, R. L., and Carter, G. W. Chapter 8. Pulmonary and Antiallergy Agents, *Annual Reports in Medicinal Chemistry*, Allen, R. C. ed., Academic Press 1988.)

U.S. Pat. No. 5,095,031 to Brooks, et. al. discloses and claims certain indole derivatives having utility for inhibiting lipoxygenase enzymes.

European Patent Application 87 311031.6 (Publication No. 0 275 667) to Gillard, et. al discloses and claims certain 3-(hetero-substituted)-N-benzylindoles as leukotriene biosynthesis inhibitors. See also 2nd International Conference on Leukotrienes and Prostanoids in Health and Disease, Oct. 9–14, 1988, Jerusalem, Israel, Abstract S5 and recently published, J. Gillard et. al., *Can. J. Physiol. Pharmacol.* 1989, 67, 456–464.

SUMMARY OF THE INVENTION

In its principal embodiment, the present invention provides certain substituted indole carboxylate derivatives which inhibit lipoxygenase enzyme activity and are useful in the treatment of allergic and inflammatory disease states in which leukotrienes play a role.

The compounds of this invention, and the pharmaceutically acceptable salts thereof have the structure

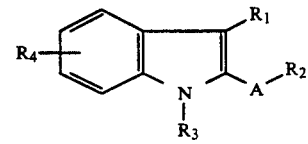

where A is selected from the group consisting of straight or branched divalent alkylene of from one to twelve carbon atoms and divalent cycloalkylene of from three to eight carbon atoms.

The group $R_1$ is selected from the group consisting of hydrogen; alkylthio of from one to six carbon atoms; phenylthio, optionally substituted with alkyl of from one to six carbon atoms, alkoxy of from one to six carbon atoms, or halogen; phenylalkylthio in which the alkyl portion contains from one to six carbon atoms, and the phenyl group is optionally substituted with alkyl of from one to six carbon atoms, alkoxy of from one to six carbon atoms, or halogen; 2-, 3-, and 4-pyridyl, optionally substituted with alkyl of from one to six carbon atoms, alkoxy of from one to six carbon atoms, or halogen; 2-, and 3-thienylthio, optionally substituted with alkyl of from one to six carbon atoms, alkoxy of from one to six carbon atoms, or halogen; 2-thiazolythio, optionally substituted with alkyl of from one to six carbon atoms, alkoxy of from one to six carbon atoms, or halogen.

The group $R_2$ is selected from —COOB where B is selected from hydrogen, a pharmaceutically acceptable cation, or a metabolically cleavable group; —COOalkyl where the alkyl portion contains from one to six carbon atoms; —COOalkyl(carbocyclic aryl) where the alkyl portion contains from one to six carbon atoms and the carbocyclic aryl portion is optionally substituted with alkyl of from one to six carbon atoms, alkoxy of from one to six carbon atoms, or halogen; —$CONR_5R_6$ where $R_5$ is selected from the group consisting of hydrogen, hydroxyl, alkyl of from one to six carbon atoms, or alkoxy of from one to six carbon atoms, and $R_6$ is selected from hydrogen or alkyl of from one to six carbon atoms; —$COR_6$; and —OH.

The group $R_3$ is selected from phenylalkyl in which the alkyl portion contains from one to six carbon atoms, and the phenyl group is optionally substituted with alkyl of from one to six carbon atoms, alkoxy of from one to six carbon atoms, or halogen; heteroarylalkyl in which the alkyl portion contains from one to six carbon atoms, and the heteroaryl portion is optionally substituted with alkyl of from one to six carbon atoms, alkoxy of from one to six carbon atoms, or halogen.

The group $R_4$ is selected from alkoxy(carbocyclic aryl) in which the alkyl portion contains from one to six carbon atoms, and the carbocyclic aryl portion is optionally substituted with alkyl of from one to six carbon atoms, alkoxy of from one to six carbon atoms, or halogen; carbocyclicaryloxy where the carbocyclic aryl portion is optionally substituted with alkyl of from one to six carbon atoms, alkoxy of from one to six carbon atoms, or halogen; heteroarylalkoxy in which the alkyl portion contains from one to six carbon atoms, and the heteroaryl portion is optionally substituted with alkyl of from one to six carbon atoms, alkoxy of from one to six carbon atoms, or halogen; and heteroaryloxy, optionally substituted with alkyl of from one to six carbon atoms, alkoxy of from one to six carbon atoms, or halogen.

In another embodiment of this invention, there are provided pharmaceutical compositions which comprise a therapeutically effective amount of a compound as defined above in combination with a pharmaceutically acceptable carrier.

In yet another embodiment of this invention, there is provided a method of inhibiting lipoxygenase enzymes in a mammal in need of such treatment comprising administering a therapeutically effective amount of a compound as defined above.

DETAILED DESCRIPTION OF THE INVENTION

Definitions of Terms

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

The term "cycloalkyl" denotes a monovalent group derived from a monocyclic or bicyclic saturated carbocyclic ring compound by the removal of a single hydrogen atom. Examples include cyclopropyl, cyclobutyl, cycopentyl, cyclohexyl, bicyclo[2.2.1]heptanyl, and bicyclo[2.2.2]octanyl.

The term "cycloalkylene" refers to a divalent group derived from a saturated carbocyclic hydrocarbon by the removal of two hydrogen atoms, for example cyclopentylene, cyclohexylene, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkyl" refers to an alkoxy group, as defined above, attached through an alkylene group to the parent molecular moiety.

The term "alkylthio" refers to an alkyl group, as defined above, attached to the parent molecular moiety through a sulfur atom and includes such examples as methylthio, ethylthio, propylthio, n-, sec- and tert-butylthio and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH2CH=CH—, —C(CH3)=CH—, —CH2CH=CHCH2—, and the like.

The term "alkynyl" refers to a divalent group derived by the removal of two hydrogen atoms from a straight or branched chain acyclic hydrocarbon group containing a carbon-carbon triple bond.

The term "alkanoyl" represents an alkyl group, as defined above, attached to the parent molecular moiety through a carbonyl group. Alkanoyl groups are exemplified by acetyl, propionyl, butanoyl and the like.

The term "carbocyclic aryl" denotes a monovalent (carbocyclic)aryl ring group derived by the removal of a single hydrogen atom from a monocyclic or bicyclic fused or non-fused ring system obeying the "4n+2 π electron" or Hückel aromaticity rule. Examples of carbocyclic aryl groups include phenyl, 1- and 2-naphthyl, biphenylyl and the like.

The term "(carbocyclic aryl)alkyl" refers to a carbocyclic ring group as defined above, attached to the parent molecular moiety through an alkylene group. Representative (carbocyclic aryl)alkyl groups include phenylmethyl or benzyl, phenylethyl, phenylpropyl, 1-naphthylmethyl, and the like.

The term "carbocyclicaryloxy" refers to a carbocyclic aryl group, as defined above, attached to the parent molecular moiety through an oxygen atom.

The term "carbocyclicarylalkoxy" refers to a carbocyclicaryl alkyl group, as defined above, attached to the parent molecular moiety through an oxygen atom.

The term "carbocyclic aryloxyalkyl" refers to a carbocyclic aryl group, as defined above, attached to the parent molecular moiety through an oxygen atom and thence through an alkylene group. Such groups are exemplified by phenoxymethyl, 1- and 2-naphthyloxymethyl, phenoxyethyl and the like.

The term "(carbocyclic aryl)alkoxyalkyl" denotes a carbocyclic aryl group as defined above, attached to the parent molecular moiety through an alkoxyalkyl group. Representative (carbocyclic aryl)alkoxyalkyl groups include phenylmethoxymethyl, phenylethoxymethyl, 1- and 2-naphthylmethoxyethyl, and the like.

"Carbocyclic arylthioalkyl" represents a carbocyclic aryl group as defined above, attached to the parent molecular moiety through a sulfur atom and thence through an alkylene group and are typified by phenylthiomethyl, 1- and 2-naphthylthioethyl and the like.

The term "carbocyclic arylaminoalkyl" refers to a carbocyclic aryl group as defined above, attached to the parent molecular moiety through a —NH-alkylene-group and is exemplified by phenylaminomethyl, phenylaminoethyl, 1- and 2-naphthylaminomethyl and the like.

The terms "heteroaryl" or "heterocyclic aryl" as used herein refers to substituted or unsubstituted 5- or 6-membered ring aromatic groups containing one oxygen atom, one, two, three, or four nitrogen atoms, one nitrogen and one sulfur atom, or one nitrogen and one oxygen atom. The term heteroaryl also includes bi-or tricyclic groups in which the aromatic heterocyclic ring is fused to one or two benzene rings. Representative heteroaryl groups are pyridyl, thienyl, indolyl, pyrazinyl, isoquinolyl, pyrrolyl, pyrimidyl, benzothienyl, furyl, benzo[b]furyl, imidazolyl, thiazolyl, carbazolyl, and the like.

The term "heteroarylalkyl" denotes a heteroaryl group, as defined above, attached to the parent molecular moiety through an alkylene group.

The term "heteroaryloxy" denotes a heteroaryl group, as defined above, attached to the parent molecular moiety through an oxygen atom.

The term "heteroarylalkoxy" denotes a heteroarylalkyl group, as defined above, attached to the parent molecular moiety through an oxygen atom.

The term "metabolically cleavable group" denotes a group which is cleaved in vivo to yield the parent molecule of the structural formulae indicated above wherein B is hydrogen. Examples of metabolically cleavable groups include —COR, —COOR, —CONRR and —CH$_2$OR radicals where R is selected independently at each occurrence from alkyl, trialkylsilyl, carbocyclic aryl or carbocyclic aryl substituted with one or more of $C_1$-$C_4$ alkyl, halogen, hydroxy or $C_1$-$C_4$ alkoxy. Specific examples of representative metabolically cleavable groups include acetyl, methoxycarbonyl, benzoyl, methoxymethyl and trimethylsilyl groups.

PREFERRED EMBODIMENTS

Specific Examples of compounds contemplated as falling within the scope of this invention include, but are not limited to the following examples:

3-[1-(4-chlorobenzyl)-3-(1,1-dimethylethylthio)-5-(pyrid-3-ylmethoxy)indol-2-yl]-2,2-dimethylpropionic acid;

3-[1-(4-chlorobenzyl)-3-(1,1-dimethylethylthio)-5-(pyrid-4-ylmethoxy)indol-2-yl]-2,2-dimethylpropionic acid;

3-[1-(4-chlorobenzyl)-3-(1,1-dimethylethylthio)-5-(pyrid-2-ylmethoxy)indol-2-yl]-2,2-dimethylpropionic acid;

3-[1-(4-chlorobenzyl)-3-(1,1-dimethylethylthio)-5-(naphth-2-ylmethoxy)indol-2-yl]-2,2-dimethylpropionic acid;

3-[1-(4-chlorobenzyl)-3-(1,1-dimethylethylthio)-5-(pyrid-2-yloxy)indol-2-yl]-2,2-dimethylpropionic acid;

3-[1-(4-chlorobenzyl)-5-(5-chlorothien-2-ylmethoxy)-3-(1,1-dimethylethylthio)-indol-2-yl]-2,2-dimethylpropionic acid;

3-[1-(4-chlorobenzyl)-3-(1,1-dimethylethylthio)-5-(4,6-dimethylpyrimid-2-ylmethoxy)indol-2-yl]-2,2-dimethylpropionic acid;

3-[1-(4-chlorobenzyl)-5-(6-chloropyrid-2-ylmethoxy)-3-(1,1-dimethylethylthio)indol-2-yl]-2,2-dimethylpropionic acid;

3-[1-(4-chlorobenzyl)-3-(1,1-dimethylethylthio)-5-(thiazol-4-ylmethoxy)indol-2-yl]-2,2-dimethylpropionic acid;

3-[1-(4-chlorobenzyl)-3-(1,1-dimethylethylthio)-5-(thien-2-ylmethoxy)indol-2-yl]-2,2-dimethylpropionic acid;

Certain compounds of the present invention may contain a basic functional group and are thus capable of forming salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, tosylate, citrate, maleate, fumarate, succinate, tartrate, naphthylate, mesylate, glucoheptonate, lactobionate, laurylsulphonate salts and the like. (See for example S. M. Berge, et al., "Pharmaceutical Salts," *J. Pharm. Sci.*, 66: 1-19 (1977) which is incorporated herein by reference)

In other cases, the compounds may contain one or more acidic functional groups such as carboxyl and the like and are capable of forming salts with pharmaceutically acceptable bases. The term "pharmaceutically acceptable salts" in these instances refers to the relatively non-toxic, inorganic and organic base addition salts of compounds of the present invention. These salts can be likewise prepared in situ during the final isolation and purification of the compounds or by separately reacting the purified compound in its free acid form with a suitable base such as the hydroxide, carbonate, or bicarbonate of a pharmaceutically acceptable metal cation or with ammonia or an organic primary, secondary, or tertiary amine. Representative alkali or alkaline earth salts include the lithium, sodium, potassium, calcium, and magnesium, salts and the like. Representative organic amines useful for the formation of base addition salts include ethylamine, diethylamine, ethylenediamine, ethanolamine, diethanolamine, piperazine, and the like. (See for example S. M. Berge, et al., "Pharmaceutical Salts," *J. Pharm. Sci.*, 66: 1-19 (1977) which is incorporated herein by reference)

Inhibition of Leukotriene Biosynthesis In Vitro

Inhibition of leukotriene biosynthesis was evaluated in assays, involving calcium ionophore-induced LTB$_4$ biosynthesis expressed by human polymorphonuclear leukocytes (PMNL) or human whole blood. Human PMNL were isolated from heparinized (20 USP units/mL) venous blood using Ficoll-Hypaque Mono-Poly Resolving Medium. Human PMNL suspensions ($5 \times 10^6$ cells/250 $\mu$L) were preincubated with test compounds or vehicle for 15 min at 37° C. followed by calcium ionophore A23187 challenge (final concentration of 8.3 $\mu$M) and the reaction terminated after 10 min by adding two volumes of methanol containing prostaglandin B$_2$ as an internal recovery standard. The methanol extracts were analyzed for LTB$_4$ content by HPLC.

The assay using human heparinized whole blood was incubated for 30 minutes at 37° C. after adding 50 μM of ionophore A23187. The plasma layer was obtained by centrifugation and deproteinized by the addition of four volumes of methanol. The methanol extract was analyzed for LTB$_4$ using a commercially available radioimmunoassay. The compounds of this invention inhibit leukotriene biosynthesis as illustrated in Table 1.

TABLE 1

Inhibition of LTB$_4$ Biosynthesis in Human PMNL and Human Whole Blood

| Example | Human PMNL IC$_{50}$ (μM) | Human Whole Blood IC$_{50}$ (μM) |
| --- | --- | --- |
| 1 | 0.017 | 1.09 |
| 2 | <0.10 | 0.84 |
| 3 | <0.05 | 0.05 |
| 4 | 0.012 | 4.42 |
| 5 | 0.015 | 2.47 |
| 6 | <0.80 | 3.20 |
| 7 | 0.030 | 1.60 |
| 8 | 0.017 | 0.11 |
| 9 | 0.0044 | 0.04 |
| 10 | 0.007 | 1.40 |

Inhibition of Leukotriene Biosynthesis In Vivo

Inhibition of the biosynthesis of leukotrienes in vivo after oral administration of compound was determined using a rat peritoneal anaphylaxis model in a similar manner as that described by Young and coworkers (Young, P. R.; Dyer, R. D.; Carter, G. W. Fed. Proc., Fed. Am. Soc. Exp. Biol. 1985, 44, 1185). In this model rats were injected intraperitoneally (ip) with rabbit antibody to bovine serum albumin (BSA) and three hours later injected ip with BSA to induce an antigen-antibody response. Rats were sacrificed 15 minutes after this challenge and the peritoneal fluids were collected and analyzed for leukotriene levels. Test compounds were administered by gavage one hour prior to the antigen challenge. Percent inhibition values were determined by comparing the treatment group to the mean of the control group. Compound 3 inhibits leukotriene biosynthesis with an ED$_{50}$ of 0.10 mg/kg po, thus, demonstrating that compounds of this invention are orally effective in preventing the in vivo biosynthesis of leukotrienes. Compounds 5, 8, and 9 inhibit >50% leukotriene biosynthesis with an oral dose of 30 μmol/kg.

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharamaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention

The compounds of the present invention are synthesized by the following general synthetic routes.

One general method for the synthesis of intermediate indoles used to prepare compounds of this invention, shown in Scheme 1, employs the Fischer indole synthesis (cf. *Advanced Organic Chemistry, Reactions, Mechanisms, and Structure*, 3rd Ed. by J. March, John Wiley and Sons, 1985, p. 1032). In this method hydrazine I is allowed to react with ketone II in a suitable solvent at ambient temperature to provide the indole intermediate III which is then converted into the hydroxyindole product IV. The intermediate IV is then treated under basic conditions with a halide V, where aryl is a heteroaryl group such as furanyl, thienyl, pyridyl, pyrimidyl, thiazolyl, benzothiazolyl, benzothiophenyl, benzofuranyl, or benzimidazolyl, with or without substitution, or aryl groups such as phenyl or naphthyl, with or without substitution, to yield indole VI. Treatment of VI with aqueous hydroxide and subsequent acidification provides the desired indole carboxylate derivative.

Scheme 1

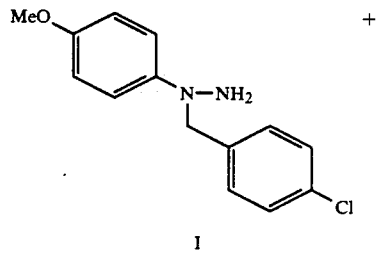

I

-continued
Scheme 1

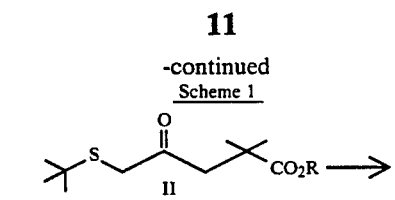

II

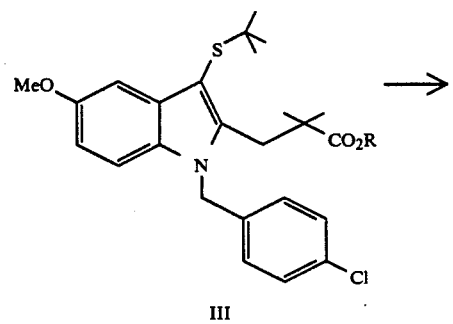

III

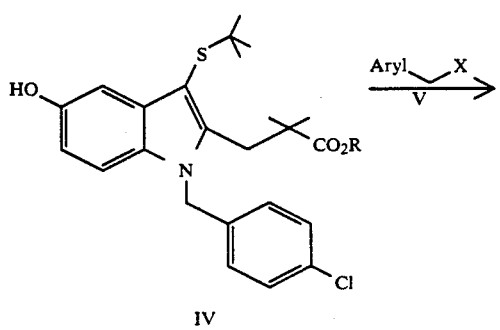

IV

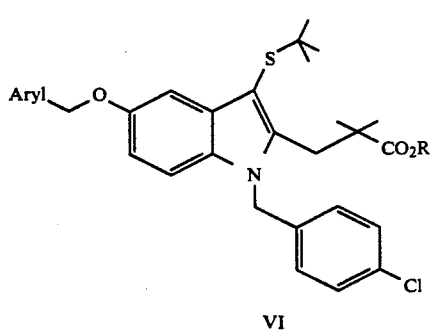

VI

Another general method illustrated in Scheme 2 involves the reaction of a hydrazine VII, where aryl is a heteroaryl group such as optionally substituted furanyl, thienyl, pyridyl, pyrimidyl, thiazolyl, benzothiazolyl, benzothiophenyl, benzofuranyl, or benzimidazolyl or optionally substituted phenyl or naphthyl with the ketone II to provide indole VI.

Scheme 2

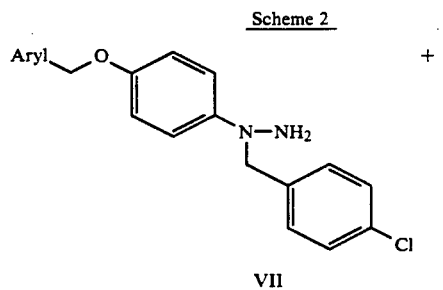

VII

-continued
Scheme 2

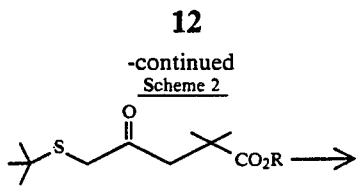

II

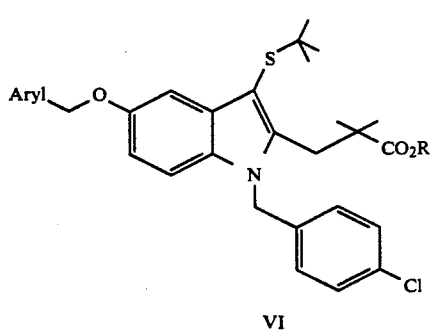

VI

The foregoing may be better understood from the following Examples, which are presented for the purpose of illustration and not intended to limit the scope of the inventive concept.

EXAMPLE 1

Preparation of 3-[1-(4-chlorobenzyl)-3-(1,1-dimethylethylthio)-5-(pyrid-3-ylmethoxy)-indol-2-yl]-2,2-dimethylpropionic acid Step 1.
1-(4-chlorobenzyl)-1-(4-methoxyphenyl)hydrazine hydrochloride Method A. To a solution of diisopropylethylamine (79.11 g; 612 mmol) in 1000 mL dichloromethane was added 4-methoxyphenylhydrazine hydrochloride (41.11 g; 235.4 mmol). This was followed by the addition of 4-chlorobenzylchloride (56.86 g; 353.1 mmol), tetrabutylammonium bromide (15.1 g; 47 mmol) and an additional 100 mL dichloromethane and the reaction was stirred for 24 hours. The mixture was then diluted with water and the layers were separated. The aqueous layer was extracted with dichloromethane. The organics were combined, dried over magnesium sulfate and concentrated. The crude residue was taken up in 2:1 toluene, diethyl ether and cooled to 0° C. HCl/dioxane (49 mL of a 4.8M solution, 235.4 mmol) was added dropwise to this solution. Upon completion of addition, the cooling bath was removed and the mixture was allowed to warm to ambient temperature and concentrated in vacuo to afford 1-(4-chlorobenzyl)-1-(4-methoxy)phenylhydrazine hydrochloride which was used with no further purification.

Method B. A solution of 4-methoxyaniline (75.0 g; 609 mmol) and 4-chlorobenzaldehyde (86.5 g; 615 mmol) in 1000 mL toluene was heated at reflux overnight with removal of water. The solvent was evaporated under reduced pressure, and the resulting light gray solid was taken up in 1500 mL tetrahydrofuran (THF). A solution of sodium cyanoborohydride (38.3 g; 609 mmol) in 180 mL methanol was added. Upon complete addition the reaction was acidified by the slow addition of acetic acid (36 mL). The reaction was stirred at ambient temperature overnight. The mixture was cooled to 0° C. and excess aqueous 6N HCl was added. The resultant precipitate was collected and washed well with diethyl ether to give N-(4-chlorobenzyl)-4-methoxyaniline hydrochloride salt as an off white solid.

A suspension of N-(4-chlorobenzyl)-4-methoxyaniline hydrochloride salt (141.4 g; 497.5 mmol), prepared as above, in 1500 mL water, 750 mL diethyl ether, and 525 mL aqueous 1N HCl was treated with a solution of sodium nitrite (37.7 g; 547 mmol) in 150 mL water. After stirring for 2 hours at ambient temperature the reaction mixture was extracted twice with diethyl ether. The combined extracts were washed with water, dried over magnesium sulfate, and concentrated to give N-nitroso-N-(4-chlorobenzyl)-4-methoxyaniline as a yellow solid.

A solution of N-nitroso-N-(4-chlorobenzyl)-4-methoxyaniline (98.7 g; 357 mmol), prepared as above, in 1200 mL THF was cooled to 0° C. and 1230 mL of a 1M solution of diisobutylaluminum hydride in hexanes was added dropwise. The ice bath was removed and the reaction was heated at reflux overnight. The reaction was cooled to ambient temperature and poured into 10% aqueous HCl. The layers were separated and the aqueous was extracted with ethyl acetate. The combined extracts were dried over magnesium sulfate and then concentrated. The crude material was dissolved in 400 mL of 1:1 ethyl acetate, hexane and treated with HCl gas. The resultant solid was collected to yield 1-(4-chlorobenzyl)-1-(4-methoxyphenyl)-hydrazine hydrochloride which was used with no further purification.

Step 2. ethyl 5-t-butylthio-2,2-dimethyl-4-oxopentanoate

To a solution of diisopropylamine (126.5 g; 1.25 mol) in 1500 mL THF at −78° C. was added n-butyllithium (500 mL of a 2.5M solution in hexanes). Upon completion of addition, the mixture was stirred for 30 minutes. A solution of ethyl isobutyrate (132 g; 1.14 mol) in 300 mL THF was added slowly over about 1 hour. The reaction was then allowed to stir for an additional hour at −78° C. 2,3-Dichloro-1-propene (138.7 g; 1.25 mol) was added dropwise. The cooling bath was removed and the reaction was stirred at ambient temperature for 15 hours. Saturated aqueous ammonium chloride solution was added and the THF was removed in vacuo. The aqueous residue was then extracted with ethyl acetate. The extracts were dried over magnesium sulfate and concentrated. Distillation yielded ethyl 4-chloro-2,2-dimethyl-4-pentenoate as a colorless liquid (b.p. 100°-104° C./30 torr).

To a solution of ethyl 4-chloro-2,2-dimethyl-4-pentenoate (170 g; 0.89 mol), prepared as above, in 750 mL ethanol and 250 mL water at 0° C. was added bromine (147 g; 0.92 mol) over a period of approximately 1 hour. When addition was complete the cooling bath was removed and the reaction was stirred at ambient temperature for 1.5 hours. The reaction was diluted with water and ethyl acetate. The layers were separated and the organic layer was washed successively with water, 1N aqueous NaOH, water, and brine. The extracts were dried over magnesium sulfate and concentrated. Distillation (b.p. 122°-152° C./30 torr) yielded a 9:1 mixture of ethyl 5-bromo-2,2-dimethyl-4-oxopentanoate and ethyl 5-chloro-2,2-dimethyl-4-oxopentanoate as a colorless oil.

A solution of the haloketone mixture (181.2 g), prepared above in 900 mL THF was cooled to 0° C. 2-Methyl-2-propylthiol (78.2 g; 0.87 mol) and triethylamine (91.5 g; 0.91 mol) were added dropwise. Upon completion of addition the cooling bath was removed and the reaction was stirred at ambient temperature for 18 hours. The mixture was filtered through celite and concentrated. Vacuum distillation afforded ethyl 5-t-butylthio-2,2-dimethyl-4-oxopentanoate (b.p. 125°-131° C./1 torr).

If methanol is used in the place of ethanol, methyl 5-t-butylthio-2,2-dimethyl-4-oxopentanoate is obtained.

Step 3. ethyl 3-[1-(4-chlorobenzyl)-3-(1,1-dimethylethylthio)-5-methoxyindol-2-yl]-2,2-dimethylpropionate 1-(4-Chlorobenzyl)-1-(4-methoxyphenyl)hydrazine hydrochloride (50 g; 190 mmol), prepared as in step 1, was dissolved in 400 mL toluene and 220 mL acetic acid. Sodium acetate (17.1 g; 210 mmol) was added followed by the addition of ethyl 5-t-butylthio-2,2-dimethyl-4-oxopentanoate (49 g; 188 mmol), prepared as in step 2. The reaction was stirred in the dark at room temperature for 4 days. The mixture was poured into water and extracted with ethyl acetate. The combined extracts were washed with water. Solid sodium bicarbonate was added to the organic extracts and the mixture was filtered. The filtrate was washed with water and brine, dried over magnesium sulfate and the solvent was removed under reduced pressure. The residue was taken up in hot ethyl acetate and filtered. The solvent was removed and the product was recrystallized from pentane to give ethyl 3-[1-(4-chlorobenzyl)-3-(1,1-dimethylethylthio)-5-methoxyindol-2-yl]-2,2-dimethylpropionate as a fluffy white solid.

Step 4. ethyl 3-[1-(4-chlorobenzyl)-3-(1,1-dimethylethylthio)-5-hydroxyindol-2-yl]-2,2-dimethylpropionate Aluminum chloride (4.1 g; 30.7 mmol) was suspended in 9 mL t-butylthiol and cooled to 0° C. Ethyl 3-[1-(4-chlorobenzyl)-3-(1,1-dimethylethylthio)-5-methoxyindol-2-yl]-2,2-dimethylpropionate (5.0 g; 10.2 mmol), prepared as in step 3, in 12 mL dichloromethane was added and the reaction mixture was stirred at 0° C. for 10 min and then at ambient temperature for 3 hours. The reaction mixture was poured into ice and acidified with 10% aqueous HCl. The mixture was extracted three times with dichloromethane. The combined extracts were rinsed with brine, dried over magnesium sulfate and concentrated. The dark brown residue was filtered through silica gel eluting with 10% diethyl ether in dichloromethane. Evaporation of the solvent afforded ethyl 3-[1-(4-chlorobenzyl)-3-(1,1-dimethylethylthio)-5-hydroxyindol-2-yl]-2,2-dimethylpropionate. m.p. 151°-152° C. $^1$H NMR (300 MHz, DMSO-$d_6$) $\delta$1.10 (t, J=7 Hz, 3H), 1.12 (s, 6H), 1.20 (s, 9H), 3.19 (bs, 2H), 4.04 (q, J=7 Hz, 2H), 5.41 (s, 2H), 6.58 (dd, J=9, 3 Hz, 1H), 6.83 (d, J=9 Hz, 2H), 6.98 (d, J=3 Hz, 1H), 7.13 (d, J=9 Hz, 1H), 7.32 (d, J=9 Hz, 2H), 8.88 (s, 1H). MS (DCI/NH$_3$) 474 (M+H)$^+$.

Step 4(a). methyl 3-[1-(4-chlorobenzyl)-3-(1,1-dimethylethylthio)-5-hydroxyindol-2-yl]-2,2-dimethylpropionate Substituting methyl 5-t-butylthio-2,2-dimethyl-4-oxopentanoate, prepared as in step 2 for ethyl 5-t-butylthio-2,2-dimethyl-4-oxopentanoate in step 3 and demethylation as described in step 4 provides methyl 3-[1-(4-chlorobenzyl)-3-(1,1-dimethylethylthio)-5-hydroxyindol-2-yl]-2,2-dimethylpropionate. $^1$H NMR (300 MHz, DMSO-$d_6$) $\delta$1.12 (s, 6H), 1.20 (s, 9H), 3.19

(bs, 2H), 3.55 (s, 3H), 5.41 (s, 2H), 6.58 (dd, J=9, 3 Hz, 1H), 6.83 (d, J=9 Hz, 2H), 6.98 (d, J=3 Hz, 1H), 7.13 (d, J=9 Hz, 1H), 7.32 (d, J=9 Hz, 2H), 8.88 (s, 1H). MS (DCI/NH$_3$) 460 (M+H)$^+$.

Step 5. ethyl 3-[1-(4-chlorobenzyl)-3-(1,1-dimethylethylthio)-5-(pyrid-3-ylmethoxy)indol-2-yl]-2,2-dimethylpropionate A suspension of ethyl 3-[1-(4-chlorobenzyl)-3-(1,1-dimethylethylthio)-5-hydroxyindol-2-yl]-2,2-dimethylpropionate (3.0 g; 6.5 mmol), prepared as in step 4, 3-picolyl chloride hydrochloride (1.1 g; 6.5 mmol), and powdered potassium carbonate (2.7 g; 19.5 mmol) in 20 mL dimethylformamide (DMF) was stirred at ambient temperature for 4 days. The reaction mixture was diluted with brine and extracted with ethyl acetate. The extracts were dried over magnesium sulfate and concentrated. The resulting residue was subjected to flash chromatography on silica gel (70% diethyl ether in hexane) to give ethyl 3-[1-(p-chlorobenzyl)-3-(1,1-dimethylethylthio)-5-(pyrid-3-ylmethoxy)indol-2-yl]-2,2-dimethylpropionate as a pale yellow oil containing a small amount of DMF.

Step 6. 3-[1-(4-chlorobenzyl)-3-(1,1-dimethylethylthio)-5-(pyrid-3-ylmethoxy)indol-2-yl]-2,2-dimethylpropionic acid A solution of ethyl 3-[1-(4-chlorobenzyl)-3-(1,1-dimethylethylthio)-5-(pyrid-3-ylmethoxy)indol-2-yl]-2,2-dimethylpropionate (3.6 g; 6.2 mmol), prepared as in step 5 in 30 mL 1:1 aqueous 1N LiOH, isopropanol was heated at 80° C. for 3 days. The reaction mixture was cooled to room temperature and the isopropanol was removed in vacuo. The residue was diluted with water and acidified to pH 5-6 by the addition of solid citric acid. The mixture was extracted with ethyl acetate. The combined extracts were dried over magnesium sulfate and concentrated. The resulting residue was chromatographed on silica gel (1% dichloromethane in diethyl ether containing 2% acetic acid to 5% dichloromethane in diethyl ether containing 2% acetic acid). Crystallization from ethyl acetate/methanol afforded 3-[1-(4-chlorobenzyl)-3-(1,1-dimethylethylthio)-5-(pyrid-3-ylmethoxy)indol-2-yl]-2,2-dimethylpropionic acid. m.p. 206°-208° C. $^1$H NMR (300 MHz, DMSO-d$_6$) δ1.08 (s, 6H), 1.15 (s, 9H), 3.17 (s, 2H), 3.18 (bs, 2H), 5.48 (s, 2H), 6.83 (m, 3H), 7.16 (d, J=3 Hz, 1H), 7.32 (m, 3H), 7.41 (dd, J=8, 5 Hz, 1H), 7.87 (m, 1H), 8.52 (dd, J=5, 2 Hz, 1H), 8.68 (d, J=2 Hz, 1H). MS (DCI/NH$_3$) 537 (M+H)$^+$. Analysis calcd for C$_{30}$H$_{33}$ClN$_2$O$_3$S: C, 67.08; H, 6.19; N, 5.22. Found: C, 66.65; H, 6.02; N, 5.11.

EXAMPLE 2

Preparation of 3-[1-(4-chlorobenzyl)-3-(1,1-dimethylethylthio)-5-(pyrid-4-ylmethoxy)-indol-2-yl]-2,2-dimethylpropionic acid The desired material was prepared according to the procedure of Example 1, steps 5 and 6, except substituting 4-picolyl chloride hydrochloride for 3-picolyl chloride hydrochloride. m.p. 238°-240° C. $^1$H NMR (300 MHZ, DMSO-d$_6$) δ1.08 (s, 6H), 1.11 (s, 9H), 3.18 (bs, 2H), 5.20 (s, 2H), 5.48 (s, 2H), 6.84 (m, 3H), 7.09 (d, J=3 Hz, 1H), 7.32 (m, 3H), 7.46 (m, 2H), 8.55 (m, 2H), 12.46 (bs, 1H). MS (DCI/NH$_3$) 537 (M+H)$^+$. Analysis calcd for C$_{30}$H$_{33}$ClN$_2$O$_3$S: C, 67.08; H, 6.19; N, 5.22. Found: C, 67.01; H, 6.23; N, 5.09.

EXAMPLE 3

Preparation of 3-[1-(4-chlorobenzyl)-3-(1,1-dimethylethylthio)-5-pyrid-2-ylmethoxy)-indol-2-yl]-2,2-dimethylpropionic acid Step 1. N-acetyl-4-(pyrid-2-ylmethoxy)aniline A mixture of 4-acetamidophenol (120 g; 796 mmol), 2-picolyl chloride hydrochloride (130.6 g; 796 mmol), and powdered potassium carbonate (330 g; 2.39 mol) in 1500 mL DMF was stirred at ambient temperature for 7 days. The reaction was poured into brine and the precipitate was collected by vacuum filtration. The solids were washed with water followed by diethyl ether. The reaction yielded N-acetyl-4-(pyrid-2-ylmethoxy)aniline as a beige solid.

Step 2. 4-(pyrid-2-ylmethoxy)aniline

A suspension of N-acetyl-4-(pyrid-2-ylmethoxy)aniline (116 g; 480 mmol), prepared as in step 1, in 1000 mL 95% ethanol and 130 mL 10M aqueous KOH was refluxed for 2 days. The reaction was concentrated and diluted with water. The mixture was extracted with ethyl acetate. The extracts were dried over magnesium sulfate and concentrated to give 4-(pyrid-2-ylmethoxy)aniline as a brown oil.

Step 3. 4-(pyrid-2-ylmethoxy)phenylhydrazine 4-(Pyrid-2-ylmethoxy)aniline (86.7 g; 433 mmol), prepared as in step 2, was suspended in 200 mL water and 108 mL concentrated HCl was added. The solution was cooled to 0° C. and sodium nitrite (30.8 g; 446 mmol) in 75 mL water was added dropwise. The reaction was stirred for 1 hour at 0° C. The diazonium salt was then transferred dropwise to a solution of sodium hydrosulfite (85% purity; 487 g; 2.80 mol) in 2000 mL water, 2000 mL diethyl ether, and 20 mL 2N aqueous NaOH at 0°-5° C. with vigorous stirring. When addition was complete 775 mL 2N aqueous NaOH was added dropwise. The cooling bath was removed and the reaction was stirred at room temperature for 1 hour. The precipitate was collected by vacuum filtration and washed with water then diethyl ether. The reaction yielded 4-(pyrid-2-ylmethoxy)phenylhydrazine as a pale green solid.

Step 4. 1-(4-chlorobenzyl)-1-[4-(pyrid-2-ylmethoxy)phenyl] hydrazine 4-(Pyrid-2-ylmethoxy)phenylhydrazine (66.2 g; 308 mmol), prepared as in step 3, was added to a solution of 86 mL diisopropylethylamine and 900 mL dichloromethane. 4-Chlorobenzyl chloride (74.4 g; 462 mmol) and tetrabutylammonium bromide (29.8 g; 92.4 mmol) and an additional 100 mL dichloromethane were added and the reaction was stirred at ambient temperature for 24 hours. The reaction mixture was diluted with water and the layers were separated. The aqueous layer was extracted with dichloromethane. The combined organics were dried over magnesium sulfate and concentrated. The residue was washed with 9:1 diethyl ether, methanol to afford 1-(4-chlorobenzyl)-1-[4-(pyrid-2-ylmethoxy)phenyl] hydrazine as a beige solid.

Step 5. methyl
3-[1-(4-chlorobenzyl)-3-(1,1-dimethylethylthio)-5-(pyrid-2-ylmethoxy)-indol-2-yl]-2,2-dimethylpropionate To a solution of methyl 5-t-butylthio-2,2-dimethyl-4-oxopentanoate (33.2 g; 135 mmol), prepared as in Example 1, step 4, in 300 mL toluene and 150 mL acetic acid was added sodium acetate (12.7 g; 155 mmol) followed by 1-(4-chlorobenzyl)-1-[4-(pyrid-2-ylmethoxy)phenyl] hydrazine (48.4 g; 143 mmol), prepared as in step 4. The reaction mixture was stirred in the dark for 5 days, then was poured into water and extracted with ethyl acetate. Solid sodium bicarbonate was added to the extracts and then filtered. The filtrate was washed with water, dried over magnesium sulfate, and the solvent was evaporated. The product was isolated by flash chromatography (40% diethyl ether in hexane) and then recystallized from ethyl acetate/hexane to yield methyl 3-[1-(4-chlorobenzyl)-3-(1,1-dimethylethylthio)-5-(pyrid-2-ylmethoxy)indol-2-yl]-2,2-dimethylpropionate.

Step 6.
3-[1-(4-chlorobenzyl)-3-(1,1-dimethylethylthio)-5-(pyrid-2-ylmethoxy)indol-2-yl]-2,2-dimethylpropionic acid A solution of methyl 3-[1-(4-chlorobenzyl)-3-(1,1-dimethylethylthio)-5-(pyrid-2-ylmethoxy)indol-2-yl]-2,2-dimethylpropionate (8.8 g; 16 mmol), prepared as in step 5, in 100 mL 1:2:1 THF, methanol, 1N aqueous LiOH was heated at reflux for 3 hours. The reaction mixture was concentrated, diluted with water, and acidified to pH 5-6 with solid citric acid. The mixture was extracted with ethyl acetate. The extracts were dried over magnesium sulfate and the solvent was evaporated. The product was recrystallized from ethyl acetate/hexane to give 3-[1-(4-chlorobenzyl)-3-(1,1-dimethylethylthio)-5-(pyrid-2-ylmethoxy)indol-2-yl]-2,2-dimethylpropionic acid as a white solid. m.p. 189°-190° C. $^1$H NMR (300 MHz, DMSO-$d_6$) $\delta$1.09 (s, 6H), 1.10 (s, 9H), 3.18 (bs, 2H), 5.20 (s, 2H), 5.47 (s, 2H), 6.85 (m, 3H), 7.09 (d, J=3 Hz, 1H), 7.32 (m, 4H), 7.49 (d, J=8 Hz, 1H), 7.79 (m, 1H), 8.57 (m, 1H). MS (DCI/NH$_3$) 537 (M+H)$^+$. Analysis calcd for $C_{30}H_{33}ClN_2O_3S$; C, 67.08; H, 6.19; N, 5.22. Found: C, 67.30; H, 6.21; N, 5.18.

EXAMPLE 4

Preparation of
3-[1-(4-chlorobenzyl)-3-(1,1-dimethylethylthio)-5-(napth-2-ylmethoxy) indol-2-yl]-2,2-dimethylpropionic acid The desired material was prepared according to the procedure of Example 1, steps 5 and 6, except substituting 2-bromomethylnaphthalene for 3-picolyl chloride hydrochloride. m.p. 213°-214° C. $^1$H NMR (300 MHz, DMSO-$d_6$) $\delta$1.09 (s, 15H), 3.18 (bs, 2H), 5.29 (s, 2H), 5.48 (s, 2H), 6.84 (m, 3H), 7.20 (d, J=2.5 Hz, 1H), 7.32 (m, 3H), 7.52 (m, 2H), 7.61 (m, 1H), 7.89-8.01 (m, 4H), 12.45 (bs, 1H). MS (DCI/NH$_3$) 586 (M+H)$^+$. Analysis calcd for $C_{33}H_{36}ClNO_3S$: C, 71.71; H, 6.19; N, 2.39. Found: C, 71.34; H, 6.26; N, 2.35.

EXAMPLE 5

Preparation of
3-[1-(4-chlorobenzyl)-3-(1,1-dimethylethylthio)-5-(pyrid-2-yloxy)indol-2-yl]-2,2-dimethylpropionic acid Step 1. N-acetyl-4-(pyrid-2-yloxy)aniline A solution of 4-acetamidophenol (20.0 g; 132.3 mmol), 2-bromopyridine (41.8 g; 265 mmol), potassium carbonate (28.3 g; 205 mmol) and Cu° (4.2 g; 66 mmol) in 130 mL pyridine was heated at reflux for 2 days. The reaction was cooled to ambient temperature and filtered through celite. The filtrate was diluted with ethyl acetate and washed with water. The extracts were dried over magnesium sulfate and the solvent was removed under reduced pressure. The material was partially purified by flash chromatography (3% methanol in dichloromethane) and then recrystallized from ethyl acetate/hexane to give N-acetyl-4-(pyrid-2-yloxy)aniline.

Step 2.
3-[1-(4-chlorobenzyl)-3-(1,1-dimethylethylthio)-5-(pyrid-2-yloxy)indol-2-yl]-2,2-dimethylpropionic acid The desired compound was prepared according to the method of Example 3, steps 2-6, except substituting N-acetyl-4-(pyrid-2-yloxy)aniline, prepared as in step 1, for N-acetyl-4-(pyrid-2-ylmethoxy)aniline. m.p. 206°-207° C. $^1$H NMR (300 MHz, DMSO-$d_6$) $\delta$1.12 (s, 6H), 1.18 (s, 9H), 3.24 (bs, 2H), 5.53 (bs, 2H), 6.86-6.99 (m, 4H), 7.08 (m, 1H), 7.28 (d, J=2.5 Hz, 1H), 7.34-7.44 (m, 3H), 7.81 (m, 1H), 8.11 (m, 1H), 12.50 (bs, 1H). MS (DCI/NH$_3$) 523 (M+H)$^+$. Analysis calcd for $C_{29}H_{31}ClN_2O_3S \cdot \frac{1}{4}H_2O$: C, 66.02; H, 6.02; N, 5.31. Found: C, 66.02; H, 5.94; N; 5.28.

EXAMPLE 6

Preparation of
3-[1-(4-chlorobenzyl)-5-(5-chlorothien-2-ylmethoxy)-3-(1,1-dimethylethylthio)indol-2-yl]-2,2-dimethylpropionic acid The desired material was prepared according to the procedure of Example 1, steps 5 and 6, except substituting 2-chloro-5-chloromethylthiophene for 3-picolyl chloride hydrochloride. m.p. 182°-184° C. $^1$H NMR (300 MHz, DMSO-$d_6$) $\delta$1.10 (s, 6H), 1.18 (s, 9H), 3.19 (bs, 2H), 5.22 (s, 2H), 5.48 (s, 2H), 6.77 (d, J=3 Hz, 1H), 6.82 (d, J=7.5 Hz, 2H), 7.01-7.07 (m, 2H), 7.18 (d, J=3 Hz, 1H), 7.29-7.35 (m, 3H), 12.46 (bs, 1H). MS (DCI/NH$_3$) 576 (M+H)$^+$, 593 (M+NH$_4$)$^+$. Analysis calcd for $C_{29}H_{31}Cl_2NO_3S_2$: C, 60.41; H, 5.42; N, 2.43. Found: C, 60.64; H, 5.49; N, 2.27.

EXAMPLE 7

Preparation of
3-[1-(4-chlorobenzyl)-3-(1,1-dimethylethylthio)-5-(4,6-dimethylpyrimid-2-ylmethoxy)indol-2-yl]-2,2-dimethylpropionic acid The desired material was prepared according to the procedure of Example 1, steps 5 and 6, except substituting 2-chloromethyl-4,6-dimethylpyrimidine, prepared according to the method of Sakamoto et al. (Sakamoto, T.; Tanji, K.; Niitsuma, S.; Ono, T.; Yamanaka, H. *Chem. Pharm. Bull.* 1980, 28, 3362), for 3-picolyl chloride hydrochloride, and substituting ethyl 5-t-butylthio-2,2-dimethyl-4-oxopentanoate prepared as in Example 1, step 4, for methyl 5-t-butylthio-2,2-dimethyl-4-oxopentanoate. m.p. 213°-215° C. $^1$H NMR (300 MHz, DMSO-$d_6$) $\delta$1.08 (s, 6H), 1.10 (s, 9H), 2.42 (s, 6H), 3.17 (bs, 2H), 5.13 (s, 2H), 5.46 (s, 2H), 6.81 (m, 3H), 7.09 (d, J=3 Hz, 1H), 7.19 (s, 1H), 7.25-7.34 (m, 3H). MS (DCI/NH$_3$) 566 (M+H)$^+$. Analysis calcd for $C_{31}H_{36}ClN_3O_3S$: C, 65.76; H, 6.41; N, 7.43. Found: C, 65.92; H, 6.43; N, 7.22.

EXAMPLE 8

Preparation of
3-[1-(4-chlorobenzyl)-5-(6-chloropyrid-2-ylmethoxy)-3-(1,1-dimethylethylthio)indol-2-yl]-2,2-dimethylpropionic acid

Step 1. 6-chloro-2-methylpyridine-N-oxide

To a solution of 6-chloro-2-methylpyridine (49.04 g; 384 mmol) in 500 mL pH 8 buffer and 300 mL THF was added cyclohexanone (3.77 g; 38.4 mmol) and Oxone ® (potassium peroxymonosulfate) (236.3 g; 384 mmol). After stirring for three days an additional portion of Oxone ® (236.3 g; 384 mmol) was added and the reaction was stirred for 24 hours. The reaction was diluted with water and extracted with ethyl acetate. The combined extracts were dried over magnesium sulfate and concentrated. The 6-chloro-2-methylpyridine-N-oxide was used with no further purification.

Step 2. 2-acetoxymethyl-6-chloropyridine

A solution of the 6-chloro-2-methylpyridine-N-oxide prepared in step 1 in 750 mL acetic anhydride was heated at reflux overnight. The reaction was cooled to ambient temperature and poured into saturated aqueous sodium bicarbonate. The mixture was diluted with ethyl acetate and filtered through celite. The layers were separated and the aqueous phase was extracted with ethyl acetate. The combined extracts were dried over magnesium sulfate and concentrated. The residue was azeotroped with benzene to remove any remaining acetic acid. 2-acetoxymethyl-6-chloropyridine was isolated by vacuum distillation (b.p. 105°–110° C./1.3 torr).

Step 3. 6-chloro-2-hydroxymethylpyridine

A solution of 2-acetoxymethyl-6-chloropyridine (17.3 g; 93.3 mmol), prepared as in step 2, in 250 mL 10% aqueous HCl was heated at reflux for 1.5 hours. The reaction mixture was cooled to room temperature and poured into 300 mL saturated aqueous sodium bicarbonate. The solution was adjusted to pH 9 by the addition of solid sodium bicarbonate. The solution was extracted with ethyl acetate. The combined extracts were dried over magnesium sulfate and concentrated. The 6-chloro-2-hydroxymethylpyridine was used with no further purification.

Step 4. 6-chloro-2-chloromethylpyridine

Thionyl chloride (12.6 mL; 173 mmol) in 100 mL chloroform was added dropwise to a solution of 6-chloro-2-hydroxymethylpyridine (13.0 g; 90.5 mmol), prepared as in step 3, in 100 mL chloroform. Upon complete addition the reaction mixture was heated at reflux for 2 hours. The reaction mixture was cooled to ambient temperature and carefully poured into 250 mL saturated aqueous sodium bicarbonate. The layers were separated and the aqueous was extracted with dichloromethane. The extracts were dried over magnesium sulfate and concentrated. 6-chloro-2-chloromethylpyridine was isolated as a pale yellow solid by flash chromatography (20% diethyl ether in hexane).

Step 5. 3-[1-(4-chlorobenzyl)-5-(6-chloropyrid-2-ylmethoxy)-3-(1,1-dimethylethylthio)indol-2-yl]-2,2-dimethylpropionic acid The desired material was prepared according to the procedure of Example 1, steps 5 and 6, except substituting 2-chloromethyl-6-chloropyridine, prepared as in step 4, for 3-picolyl chloride hydrochloride and substituting ethyl 5-t-butylthio-2,2-dimethyl-4-oxopentanoate, prepared as in Example 1, step 4, for methyl 5-t-butylthio-2,2-dimethyl-4-oxopentanoate. m.p. 206°–207° C. $^1$H NMR (300 MHz, DMSO-d$_6$) δ1.09 (s, 6H), 1.10 (s, 9H), 3.18 (bs, 2H), 5.19 (s, 2H), 5.48 (bs, 2H), 6.80–6.88 (m, 3H), 7.07 (d, J=2.5 Hz, 1H), 7.30–7.36 (m, 3H), 7.45 (d, J=8 Hz, 1H), 7.50 (d, J=8 Hz, 1H), 7.86 (t, J=8 Hz, 1H), 12.48 (bs, 1H). MS (DCI/NH$_3$) 571 (M+H)$^+$, 588 (M+NH$_4$)$^+$. Analysis calcd for C$_{30}$H$_{32}$Cl$_2$N$_2$O$_3$S: C, 63.04; H, 5.64; N, 4.90. Found: C, 63.19; H, 5.64; N, 4.77.

EXAMPLE 9

Preparation of
3-[1-(4-chlorobenzyl)-3-(1,1-dimethylethylthio)-5-(thiazol-4-ylmethoxy)indol-2-yl]-2,2-dimethylpropionic acid

Step 1. Thioformamide

To a vigorously stirring solution of formamide (26.5 mL; 665 mmol) in 300 mL THF was added phosphorus pentasulfide (30.4 g; 68.4 mmol). A cooling bath was used to maintain the internal temperature between 30°–35° C. After complete addition the reaction was stirred for 6 hours. The mixture was filtered through celite and evaporated to afford thioformamide as a pale yellow oil which solidified upon cooling.

Step 2. 4-chloromethylthiazole hydrochloride

To the thioformamide from step 1 (20.4 g; 334 mmol) in 300 mL acetone was added 1,3-dichloroacetone (36.9 g; 291 mmol). The reaction was stirred at room temperature for 5 days. The mixture was filtered and the precipitate was sublimed (100°–110° C.) to give 4-chloromethylthiazole hydrochloride as a white solid.

Step 3. 3-[1-(4-chlorobenzyl)-3-(1,1-dimethylethylthio)-5-(thiazol-4-ylmethoxy)indol-2-yl]-2,2-dimethylpropionic acid The desired material was prepared according to the procedure of Example 1, steps 5 and 6, except substituting 4-chloromethylthiazole hydrochloride, prepared as in step 2, for 3-pocolyl chloride hydrochloride and substituting ethyl 5-t-butylthio-2,2-dimethyl-4-oxopentanoate, prepared as in Example 1, step 4, for methyl 5-t-butylthio-2,2-dimethyl-4-oxopentanoate. m.p. 194°–195° C. $^1$H NMR (300 MHz, DMSO-d$_6$) δ1.10 (s, 6H), 1.18 (s, 9H), 3.19 (bs, 2H), 5.22 (s, 2H), 5.49 (s, 2H), 6.80–6.87 (m, 3H), 7.19 (d, J=2.5 Hz, 1H), 7.29–7.35 (m, 3H), 7.73 (m, 1H), 9.11 (d, J=2.5 Hz, 1H), 12.47 (bs, 1H). MS (DCI/NH$_3$) 543 (M+H)$^+$, 560 (M+NH$_4$)$^+$. Analysis calcd for C$_{28}$H$_{31}$ClN$_2$O$_3$S$_2$: C, 61.92; H, 5.72; N, 5.16. Found: C, 61.58; H, 5.65; N, 5.10.

EXAMPLE 10

Preparation of
3-[1-(4-chlorobenzyl)-3-(1,1-dimethylethylthio)-5-(thien-2-ylmethoxy)indol-2-yl]-2,2-dimethylpropionic acid

Step 1. 2-bromomethylthiophene

To a solution of 2-hydroxymethylthiophene (15.6 g; 137 mmol) in 30 mL dichloromethane at 0° C. was added a solution of phosphorus tribromide in dichloromethane (46 mL of a 1M solution). The reaction mixture was stirred for 30 min at 0° C. and then 30 min at ambient temperature. The mixture was poured over ice and extracted with diethyl ether. The extracts were washed with brine, dried over magnesium sulfate and evaporated to give a dark green liquid. 2-bromomethylthiophene was isolated as a colorless liquid by short-path distillation (b.p. 58° C./2 torr).

Step 2.
3-[1-(4-chlorobenzyl)-3-(1,1-dimethylethylthio)-5-(thien-2-ylmethoxy)indol-2-yl]-2,2-dimethylpropionic acid The desired material was prepared according to the procedure of Example 1, steps 5 and 6, except substituting 2-bromomethylthiophene, prepared as in step 1 for 3-picolyl chloride hydrochloride and substituting ethyl 5-t-butylthio-2,2-dimethyl-4-oxopentanoate, prepared as in Example 1, step 4, for methyl 5-t-butylthio-2,2-dimethyl-4-oxopentanoate. m.p. 204°–205° C. $^1$H NMR (300 MHz, DMSO-$d_6$) δ1.05 (s, 6H), 1.14 (s, 9H), 3.13 (bs, 2H), 5.22 (s, 2H), 5.42 (bs, 2H), 6.73 (d, J=3 Hz, 1H), 6.78 (d, J=8 Hz, 2H), 6.98 (d, J=5 Hz, 1H), 6.99 (d, J=5 Hz, 1H), 7.15 (d, J=3 Hz, 1H), 7.22–7.30 (m, 3H), 7.48 (dd, J=5, 2 Hz, 1H), 12.40 (bs, 1H). MS (DCI/NH$_3$) 542 (M+H)$^+$, 559 (M+NH$_4$)$^+$. Analysis calcd for $C_{29}H_{32}ClNO_3S_2$: C, 64.24; H, 5.87; N, 2.50. Found: C, 64.25; H, 5.95; N, 2.58.

We claim:

1. A compound having the structure

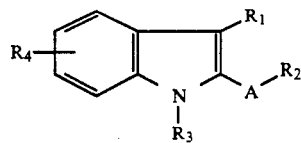

or a pharmaceutically acceptable salt thereof wherein
A is selected from the group consisting of straight or branched divalent alkylene of from one to twelve carbon atoms and divalent cycloalkylene of from three to eight carbon atoms;
$R_1$ is selected from the group consisting of
hydrogen,
alkylthio of from one to six carbon atoms,
phenylthio, optionally substituted with alkyl of from one to six carbon atoms, alkoxy of from one to six carbon atoms, or halogen,
phenylalkylthio in which the alkyl portion contains from one to six carbon atoms, and the phenyl group is optionally substituted with alkyl of from one to six carbon atoms, alkoxy of from one to six carbon atoms, or halogen,
$R_2$ is selected from the group consisting of
—COOB wherein B is selected from hydrogen, a pharmaceutically acceptable cation, or a metabolically cleavable group,
—COOalkyl where the alkyl portion contains from one to six carbon atoms,
—COOalkylcarbocyclicaryl where the alkyl portion contains from one to six carbon atoms and the aryl portion is optionally substituted with alkyl of from one to six carbon atoms, alkoxy of from one to six carbon atoms, or halogen,
—CONR$_5$R$_6$ wherein
$R_5$ is selected from the group consisting of hydrogen, hydroxyl, alkyl of from one to six carbon atoms, and alkoxy of from one to six carbon atoms, and
$R_6$ is selected from the group consisting of hydrogen and alkyl of from one to six carbon atoms,
—COR$_6$, and
—OH;
$R_3$ is selected from the group consisting of
phenylalkyl in which the alkyl portion contains from one to six carbon atoms, and the phenyl group is optionally substituted with alkyl of from one to six carbon atoms, alkoxy of from one to six carbon atoms, or halogen,
$R_4$ is selected from the group consisting of
thiazolylalkyloxy in which the alkyl portion contains from one to six carbon atoms, and the heteroaryl portion is optionally substituted with alkyl of from one to six carbon atoms, alkoxy of from one to six carbon atoms, or halogen, and
thiazolyloxy optionally substituted with alkyl of from one to six carbon atoms, alkoxy of from one to six carbon atoms, or halogen.

2. A compound or pharmaceutically acceptable salt thereof as defined in claim 1 wherein $R_2$ is —COOB and B is as defined therein.

3. A compound or pharmaceutically acceptable salt thereof as defined in claim 2 wherein A is

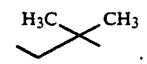

4. A compound or pharmaceutically acceptable salt thereof as defined in claim 3 wherein $R_1$ is alkylthio of from one to six carbon atoms.

5. A compound or pharmaceutically acceptable salt thereof as defined by claim 1 wherein $R_4$ is thiazolymethoxy, optionally substituted with alkyl of from one to six carbon atoms, alkoxy of from one to six carbon atoms, or halogen.

6. A compound or pharmaceutically acceptable salt thereof as defined by claim 1 selected from the group consisting of:
3-(1-(4-chlorobenzyl)-3-(1,1-dimethylethylthio)-5-(thiazol-4-ylmethoxy)indol-2-yl)-2,2-dimethylpropionic acid.

7. A pharmaceutical composition for inhibiting the biosynthesis of leukotrienes comprising a therapeutically effective amount of a compound as defined by claim 1 in combination with a pharmaceutically acceptable carrier.

* * * * *